United States Patent [19]

Teale et al.

[11] Patent Number: 5,167,955

[45] Date of Patent: Dec. 1, 1992

[54] **NEW AGGREGATION PHEROMONE FOR THE BARK BEETLE *IPS PINI* AND USES THEREOF**

[75] Inventors: Stephen A. Teale; Francis X. Webster; Aijun Zhang, all of Syracuse, N.Y.

[73] Assignee: The Research Foundation of State University of New York, Albany, N.Y.

[21] Appl. No.: 702,055

[22] Filed: May 17, 1991

[51] Int. Cl.$^5$ ............................................. A01N 31/06
[52] U.S. Cl. ..................................... 424/84; 568/377
[58] Field of Search ........................... 568/377; 424/84

[56] References Cited

U.S. PATENT DOCUMENTS

| | | | |
|---|---|---|---|
| 3,755,563 | 8/1973 | Vite | 424/84 |
| 3,840,023 | 10/1974 | Demole | 426/175 |
| 3,989,857 | 11/1976 | Demole | 426/536 |
| 4,034,080 | 7/1977 | Silverstein | 424/84 |
| 4,179,446 | 12/1979 | Tumlinson | 424/84 |
| 4,291,051 | 9/1981 | Wilson | 424/278 |
| 4,357,339 | 11/1982 | Wilson | 424/273 |
| 4,474,991 | 10/1984 | Guss | 568/382 |
| 4,565,695 | 1/1986 | Guss | 424/84 |
| 4,839,383 | 6/1989 | Vite | 424/84 |
| 4,871,537 | 10/1989 | Chuman | 424/84 |
| 4,990,331 | 2/1991 | Slessor | 424/84 |
| 4,992,268 | 2/1991 | Landolt | 424/77 |

OTHER PUBLICATIONS

Laitalainen et al, J. Chem. Soc., Perkin Trans 1, pp. 333–340 (1983).
Frimer et al, Tet. Lett., vol. 23, #12, pp. 1301–1304 (1982).
Birch et al, J. Chem. Ecol., vol. 6, pp. 703–717 (1980).
Lanier et al, J. Chem. Ecol., vol. 6, pp. 677–687 (1980).

*Primary Examiner*—James H. Reamer
*Attorney, Agent, or Firm*—Heslin & Rothenberg

[57] ABSTRACT

The invention provides a new aggregation pheromone for the bark beetle *Ips pini* identified as lanierone. Lanierone is the compound 4,4,6-trimethyl-2-hydroxy-2,5-cyclohexadiene-1-one and can be used, for example, to attract or trap bark beetles for monitoring or controlling the reproduction of the bark beetles.

10 Claims, 11 Drawing Sheets

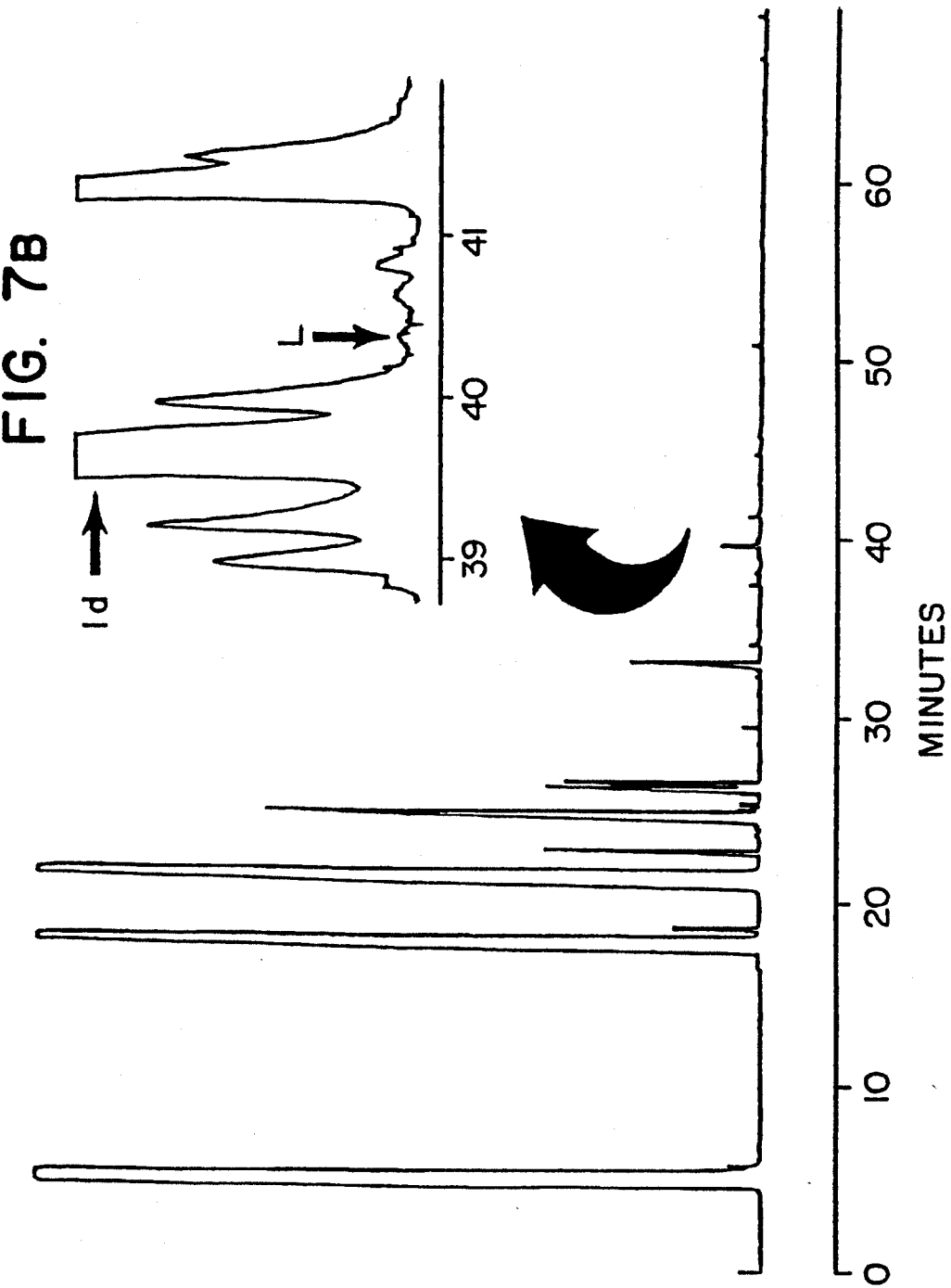

NEW AGGREGATION PHEROMONE FOR THE BARK BEETLE *IPS PINI* AND USES THEREOF

This invention was made with support under National Science Foundation Grant Nos. DCB8608077 and DIR8821239, and U.S. Department of Agriculture Grant No. 8837253-3974. Accordingly, the U.S. Government has certain rights in the invention.

BACKGROUND OF THE INVENTION

1. Technical Field

This invention relates to a pheromone, and more particularly, to the new aggregation pheromone for the bark beetle *Ips pini*, lanierone (4,4,6-trimethyl-2-hydroxy-2,5-cyclohexadiene-1-one).

2. Description of the Prior Art

Throughout this application various publications are referenced by arabic numerals within parentheses. Full citations for these references may be found at the end of the specification immediately preceding the claims. The disclosures of these publications in their entireties are hereby incorporated by reference in this application in order to more full describe the state of the art to which the invention pertains.

The pine engraver, *Ips pini* Say, breeds in pines and spruces throughout most of North America. Upon locating a host tree, males bore into the phloemcambium region and release a chemical attractant (pheromone). *Ips pini* kills pines and spruces throughout North America, therefore, a means of controlling this pest is highly desirable.

The mass attacks on host trees by these insects is known to be guided, at least in part, by the pheromones emitted by the insects. These pheromones act as aggregating agents to attract other beetles of the species to a food supply and to mating opportunities. Exploitation of the insects reliance on an aggregation pheromone to bring the sexes together offers intriguing possibilities for insect control.

A number of economically important insects are currently monitored, partially controlled, or completely controlled by use of their own specific pheromone. The use of pheromones has also been reported for locating, surveying, or monitoring pest populations at levels not otherwise detectable. The following U.S. Patents, for example, disclose insect pheromones and their uses: U.S. Pat. No. 4,034,080, issued Jul. 5, 1977 to Silverstein et al. (European Bark Beetle); U.S. Pat. No. 4,179,446, issued Dec. 18, 1979 to Tumlinson, III et al. (Japanese Beetle); U.S. Pat. No. 4,291,051, issued Sep. 22, 1981 and U.S. Pat. No. 4,357,339, issued Nov. 2, 1982, both to Wilson et al. (Pine Beetles); U.S. Pat. No. 4,990,331, issued Feb. 5, 1991 to Slessor et al. (Honey Bees); U.S. Pat. No. 4,992,268, issued Feb. 12, 1991 to Landolt et al. (Papaya Fruit Fly); U.S. Pat. No. 4,474,991, issued Oct. 2, 1984 and U.S. Pat. No. 4,565,695, issued Jan. 21, 1986, both to Guss et al. (Southern Corn Rootworm); and U.S. Pat. No. 4,871,537, issued Oct. 3, 1989 to Chuman et al. (Banded Cucumber Beetle).

In the case of *Ips pini*, the aggregation pheromone was reported to consist of a single compound, ipsdienol (1,10). More recently, Greis et al. (7) reported that *I. pini* in British Columbia produce E-myrcenol and Miller et al. (14) reported that E-myrcenol was behaviorally active for *I. pini* in British Columbia. In addition, β-phellandrene, a major constituent of the terpene fraction of lodgepole pine oleoresin (*Pinus contorta* var. latifolia Engelmann) is attractive to *I. pini* in British Columbia (13).

Interpopulational pheromonal specificity (8) has been reported to be based on ipsdienol enantiomeric composition (1,10). In general, western populations produce and respond to blends of over 90% (−)-ipsdienol [less than 10% (+)] and eastern populations produce and respond to a nearly racemic mixture of ipsdienol [roughly 50:50 (−):(+)]. The specificity of response to pheromones can also vary seasonally within a population. A New York population of *I. pini* responded in the spring and early summer to natural pheromone sources but not to racemic ipsdienol, while in the later summer and fall the number of beetles trapped by ipsdienol and natural sources were not significantly different. In addition, laboratory reared beetles originating in New York are attracted to a pheromone extract, but not to ipsdienol in laboratory bioassays. This demonstrates that one or more additional compounds are required for response.

The identification of the additional component(s) of the bark beetle pheromone is necessary in order to use the pheromone to control these insect pests. To this end, applicants have isolated and identified a new pheromone component for *I. pini* through the use of the fractionation and bioassay method of Silverstein et al. (16). The new component is a new natural product and is designated "lanierone," in recognition of the late Gerald N. Lanier and his valuable contributions to bark beetle chemical ecology.

SUMMARY OF THE INVENTION

Applicants have for the first time obtained in pure, or in substantially pure form, a second male-produced component of the pheromone of the bark beetle, *Ips pini*. This new compound, identified as the compound lanierone, helps to provide a sensitive tool for detection of the bark beetle and a means for population control and population density estimation of this pest. Its usefulness in eliciting a behavioral response when applied to a locus suggests the following economic applications: (1) the detection of infestation outbreaks, (2) the monitoring of existing adult populations in order to predict infestation levels the following year, for scheduling of treatment with viable insecticides, and (3) control of reproduction in adult populations either by direct disruption of mating through confusion or inhibitory properties, or by attracting a demographically significant portion of the insect population for subsequent destruction or sterilization.

In accordance with this discovery, it is an object of the invention to identify a unique pheromone from the bark beetle, *Ips pini*. It is also an object of the invention to produce 4,4,6-trimethyl-2-hydroxy-2,5-cyclohexadiene-1-one as a synthetic pheromone of the bark beetle.

A further object of the invention is to utilize 4,4,6-trimethyl-2-hydroxy-2,5-cyclohexadiene-1-one as a detection, monitoring, or control agent for this major agricultural pest.

Another object of the invention is to provide a bark beetle pheromone for use with insecticides, biological control agents, and the like to attract and combat the pest. Other objects and advantages of this invention will become readily apparent from the ensuing description.

Lanierone, (4,4,6-trimethyl-2-hydroxy-2,5-cyclohexadiene-1-one) was isolated and identified from a Porapak Q collection of volatiles from male *Ips pini* from New York through a GC fractionation and bioassay sequence. In both the laboratory and the field, synthetic lanierone, in a 1:100 ratio with synthetic ipsdienol, is as attractive as natural pheromone sources. Synthetic ipsdienol alone is not attractive in the laboratory and only weakly attractive in the field. Varying the ratio of lanierone to ipsdienol in the field from $10^{-4}:1$ to 1:1 in ten fold increments resulted in an increased number of beetles trapped at the three lower ratios, but also in an increase in the proportion of males trapped. In the field, all combinations of lanierone to ipsdienol attracted proportionately fewer males than did pheromone-producing male beetles. GC and GC-MS analyses of Porapak Q trapped volatiles revealed that lanierone is produced in an amount equal to about 0.2% of that of ipsdienol and is produced exclusively by males. The small amount of lanierone produced, together with a GC retention time similar to that of ipsdienol on a nonpolar column, probably confounded its detection in earlier studies.

BRIEF DESCRIPTION OF THE DRAWINGS

These and other objects, advantages and features of the present invention will be more fully understood from the following detailed description of certain embodiments thereof when considered in conjunction with the accompanying drawings in which:

FIG. 7 is GC tracings of volatiles from 1250 male *I. pini* boring in red pine collected on Porapak Q (Aeration 2; see text for details). Normal scale and 100× (inset).

DETAILED DESCRIPTION OF THE INVENTION

Figure 1:
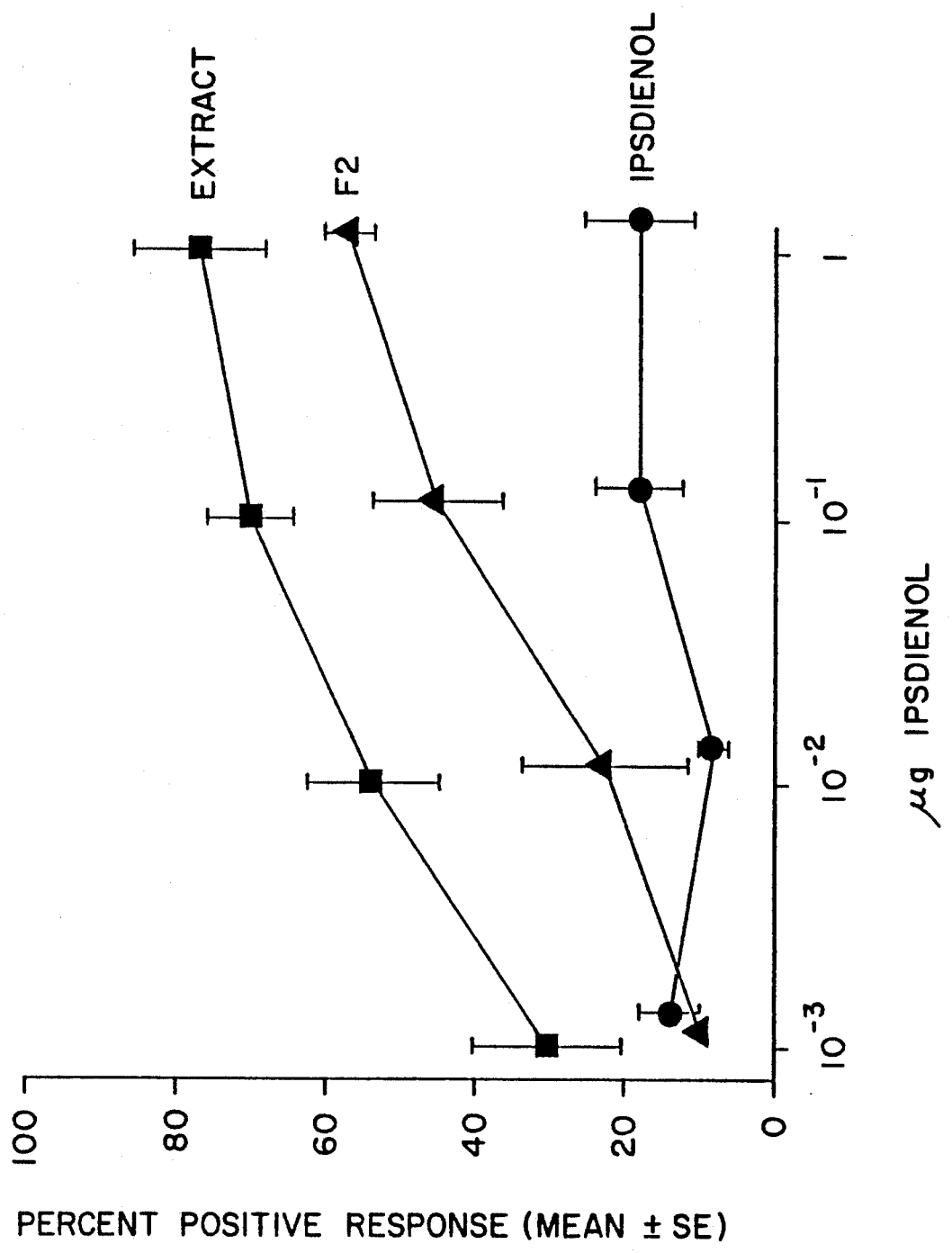
FIG. 1 is the percent positive response by female *I. pini* in laboratory bioassays of OV-101 fraction 2 (F2), starting extract (Aeration 1), and synthetic racemic ipsdienol. (N=30 beetles at each concentration; concentrations are µg ipsdienol). Stars indicate significant differences between means (P<0.05; LSD test).

The compound of the invention "lanierone", 4,4,6-trimethyl-2-hydroxy-2,5-cyclohexadiene-1-one, is characterized by the following structural formula:

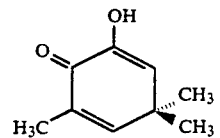

The subject invention provides synthetic compositions comprising lanierone and a suitable carrier, and preferably further comprising ipsdienol, 2-methyl-6-methylene-octa-2,7-dien-4-ol. Ipsdienol enantiomers have the following structural formulas:

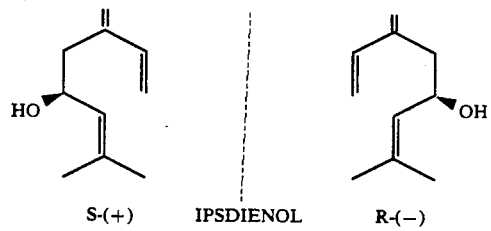

Preferably, the ratio of the amount of lanierone to the amount of ipsdienol is an amount effective to control or attract bark beetles, such as a ratio of about 1:100.

The pure or substantially pure pheromone (preferably, in combination with ipsdienol) may be used as a detecting agent, monitoring agent, or control agent for adult beetles. In practice, lanierone is used as a trap bait, or is otherwise applied to a locus of the adults, in an amount effective to induce the desired response. In the case of an attractant response, for example, an effective amount is defined as that quantity of compound which provides a release rate of the compound that attracts beetles to the location of the bait at a rate significantly higher than beetles are attracted to a non-baited location. Factors such as population density, temperature, wind velocity and release rate will influence the response of the beetles and thus the actual number of beetles trapped. Factors such as temperature, wind velocity and the type of pheromone disseminator will influence release rate. The amount of compound in a particular set of circumstances that will provide a release rate within an effective range can readily be determined by a dose response field test.

In the case where the desired response is disruption of mating by confusing or inhibiting the beetles, an effective amount is defined as that quantity of compound which provides a release rate of the compound that permeates the atmosphere such that male beetles are prevented from orienting to and inseminating the female beetles at a rate significantly higher than disruption of mating at a non-treated location. As with the attractant response, factors such as population density, temperature, wind velocity and release rate will influence the actual number of beetles disrupted. The exact dose to use in any particular set of circumstances can readily be determined by a dose response field test.

It is envisioned that lanierone would be useful in detecting, monitoring, or controlling bark beetle populations when used in conjunction with a trap or pheromone disseminator as known in the art. Exemplary of such a trap are funnel and sticky traps. Illustrative of pheromone disseminators are rubber septa and capillaries. Typically, the compound is applied to the device in solution with hexane or another suitable carrier. When used as a detection or monitoring agent, traps are baited with the compound of the invention and the catch tabulated to determine size and location of infestation. Economic use of appropriate pest management systems can then be determined.

Use of the pheromone as a control agent can be carried out in several ways. One method is to use the compound to attract the insects to suitable substrates and subsequently or simultaneously expose the beetles to insecticides which control the beetles. An effective amount of the insecticide is used, that is, an amount that is lethal for an exposed insect, or at least sublethal but sufficient to incapacitate the insect in regard to mating activity. Insecticides can be used in traps baited with the pheromone. This eliminates the need to spread the insecticides unnecessarily. It is also envisioned that chemosterilants could be used in conjunction with the pheromone compound to attract and sterilize the beetles.

Another method to control beetles using the compound is to detect the location and boundaries of localized beetle infestations and employ in the area biological control agents, such as parasites or predators of the bark beetle.

Other uses of the compound will be obvious to those in the art.

Applicants' results demonstrate that the principle male-produced pheromone components of *Ips pini* in New York are racemic ipsdienol and lanierone (4,4,6-trimethyl-2-hydroxy-2,5-cyclohexadiene-1-one). The bioassay of the starting extract showed that attractive volatiles were collected in the aeration of male beetles on Porapak Q. The attractiveness was retained during fractionation, and the fraction (F3) that contained lanierone was attractive in combination with synthetic ipsdienol but not alone. Furthermore, laboratory bioassays and field experiments demonstrated that only the combined mixture was as attractive as natural pheromone. Ipsdienol alone is not attractive in laboratory bioassays. Thus, lanierone and ipsdienol have a synergistic, or multiplicative effect.

The amount of lanierone produced is small relative ipsdienol. Applicants isolated only about 5 μg lanierone and about 20 mg ipsdienol from the starting material. However, because applicants' GC collection efficiency was less than 100%, there must have been more lanierone present in the starting material. The GC analysis of Aeration 2 (FIG. 7), which was not fractionated, showed that the proportion of lanierone to ipsdienol is about 1:500. Byers et al. (4) reported a similar situation in the scolytid *Pityogenes chalcographus* (L.) in which one component, methyl decadienoate (E,Z-MD), is present as a minute fraction of another, chalcogran. The cryptic nature of pheromone components like E,Z-MD and lanierone emphasizes the importance of the fractionation and bioassay method (16) for identifying pheromone components from complex mixtures of plant and insect compounds. Another method is the differential diagnosis of Vité and Renwick (22) or variations thereof (e.g., 7, 18). In this method, GC traces of attractive and nonattractive extracts are compared and the peaks that are unique to the attractive extract are considered potential pheromone components. This method can be used to detect pheromone components, but only if they do not co-elute with other peaks, and if the peaks are reasonably large. Lanierone in *I. pini* presents an ideal example of a situation that would be extremely difficult to resolve by differential diagnosis methods. Lanierone co-elutes with ipsdienol on at least one non-polar GC column and its peak is only about 0.2% as large as that of ipsdienol.

Applicants' isolation of lanierone represents the first isolation of this compound from a natural source and lanierone is the only known scolytid pheromone component with a carotenoid structure. Birgersson et al. (2) reported the presence of a reduced form of lanierone, β-isophorone, in the hindguts of *I. typographus* females. However, its behavioral significance, if any, is unknown.

The sex ratio differences among responders to synthetic (lanierone plus ipsdienol) and natural (20 males in red pine) baits suggest that other factors may be important in the host colonization process. Using a differential diagnosis technique, Greis et al. (7) found that E-myrcenol is produced by *I. pini* in British Columbia. Miller et al. (14) found that E-myrcenol had an inhibitory effect on attraction by *I. pini* in British Columbia when released with ipsdienol. (In contrast to the New York population, *I. pini* in British Columbia are attracted to synthetic ipsdienol in Jul. [14]). Higher release rates of E-myrcenol, in combination with a fixed amount of ipsdienol, attracted more males than the lower release rates, but the experiments were conducted consecutively so it was not possible to exclude the possibility that the sex ratios of flying beetles were different during the two experiments (14). In addition, when E-myrcenol was placed on freshly cut lodgepole pine logs, the increase in the number of *I. pini* colonizing the log was proportional to the amount of E-myrcenol released (14). More experiments are needed to evaluate interactions between ipsdienol, lanierone, E-myrcenol and the kairomone, β-phellandrene (13) as well as geographic variation in the use of these compounds.

The fact that neither of two previous investigations (1,10) into the chemical identification of the pheromone of *I. pini* had found lanierone is perplexing. In addition, applicants' findings that ipsdienol alone is not attractive in laboratory bioassays nor in the field in the spring and early summer appears contradictory with the reports of Birch et al. (1), Lanier et al. (10) and Miller et al. (14) in which ipsdienol alone was reported to be attractive. Birch et al. (1) and Lanier et al. (10) utilized the rigorous fractionation and bioassay method (16) which is the only insect pheromone identification method that logically will allow only the least behaviorally active components to be overlooked. This made the apparent incongruity between applicants' results and those of Lanier et al. (10) and Birch et al. (1) especially difficult to reconcile.

Three factors interacted to make the detection and isolation of lanierone difficult: (1) the similar retention times of ipsdienol and lanierone, (2) the small quantity required for response, and (3) seasonal variation in response to pheromone. Together, they explain why lanierone was not detected by Lanier et al. (10). First, the incomplete separation of ipsdienol and lanierone that applicants observed on OV-101, as indicated by laboratory bioassay of Fraction 2, suggests that Lanier et al. (10) may not have achieved complete separation of ipsdienol and lanierone. Lanier et al. (10) used apparently pure, natural ipsdienol in the laboratory, but applicants suggest that it could have contained lanierone which would have caused an apparent response to ipsdienol. Positive response to synthetic ipsdienol in the lab bioassays of Lanier et al. (10) is more difficult to explain. It is possible that the less stringent scoring method (9) produced false positives, that the air flow rates of the Moeck (15) olfactometer were not equal, which could cause differential anemotaxis, that their release rates could have been very high (no quantitative measure of ipsdienol delivery rate or dosage was given), or that their synthetic ipsdienol was inadvertently contaminated with natural lanierone.

Lanier et al. (10) tested the attractiveness of synthetic ipsdienol in the field and observed a level of response equivalent to twenty male beetles boring in red pine. Attraction to synthetic material under natural field conditions is often considered the final, conclusive test of a pheromone identification (16,21). Yet, the response of *I. pini* to pheromone can vary during the flight period. In the spring and early summer, *I. pini* only responded to male beetles and not to synthetic ipsdienol. In the late summer and fall, there was no significant difference between the numbers of beetles attracted to synthetic ipsdienol and male beetles. This seasonal variation in response to pheromone is associated with population density which is usually highest in late summer and fall. Lanier et al. (10) conducted field tests of synthetic ipsdienol in Aug. and Sep. when *I. pini* frequently responds to an incomplete component blend (i.e., ipsdienol). Stewart (19) described the field site of Lanier et al. (10) as having been thinned in the spring of the year previous to the field test. If Lanier et al. (10) had conducted their field tests in the spring or at a lower density site (undisturbed), they probably would not have observed attraction to synthetic ipsdienol.

There is no a priori contradiction between applicants' results and those of Birch et al. (1) and Miller et al. (14). In view of the differences in ipsdienol stereochemistry between New York and western populations, the possibility of geographic variation in the presence of lanierone cannot be ruled out. It is not known if lanierone is produced by the California population, and unless this is demonstrated, there is no inherent incongruity between applicants' results and those of Birch et al. (1).

The role of lanierone is the key to understanding seasonal variation in response to ipsdienol in New York. Because variation in response to ipsdienol is dependent on population density, production of lanierone probably does not vary significantly with season. This can now be determined by direct measurement.

MATERIALS AND METHODS

Insect rearing. Beetles used for pheromone collection, laboratory bioassays, and in bait-logs for field experiments were reared in a laboratory colony originating in red pine (*Pinus resinosa* Ait.) 25 km south of Syracuse, New York in 1973. Beetles captured at the original locality were periodically added to the colony to prevent inbreeding. Fresh red pine logs were sealed at the ends with hot wax and placed in the colony weekly. Beetles were collected by placing infested logs in metal containers (40 cm dia $\times$ 60 cm) fitted with glass collection jars (1 liter). For bioassay, beetles were removed and used within 24 hours of emergence. For pheromone collections, beetles were collected daily, sexed, and then stored on damp toweling at 5° C. for up to two weeks.

Pheromone collection. Two large collections of volatiles were made by introducing individual, male beetles into the phloem of fresh red pine logs (about 15 cm $\times$ 1 m) through cork borer holes (5 mm dia.) covered with aluminum screen patches. The infested logs were placed in a metal container (152 cm $\times$ 43 cm $\times$ 69 cm) and aerated with charcoal filtered air. Volatiles were trapped on two Porapak Q (5) filters (50 ml each) connected in series. The volatiles were extracted from the Porapak Q with pentane (100 ml, combined) and the pentane solution was concentrated by distillation.

The purpose of the first aeration (Aeration 1) was to obtain a large amount of active material for factionation and bioassay (16). Male beetles (1040) were aerated (4 liters/min) for 168 hr. The second aeration (Aeration 2) was used to quantify production of ipsdienol and lanierone, and for use in laboratory and field biossays comparing natural and synthetic materials. Male beetles (1250) were aerated 1 liter/min) for 80 hrs.

To determine the origin of lanierone, males and females (150 each) were simultaneously aerated for 105 hr in separate glass columns (15 cm interior dia. $\times$ 50 cm) while boring in red pine logs (12 cm dia. $\times$ 48 cm) cut from adjacent sections of a single tree. Volatiles were collected separately on Porapak Q (50 ml). Due to the small quantity of lanierone in the male aeration, both extracts were analyzed by GC-MS using selective ion monitoring (m/z 109).

Fractionation. The concentrated Porapak Q extract from the first aeration was sequentially fractionated on four packed columns in a Varian Aerograph Series 2700 gas chromatograph with a splitter (3) and flame ionization detector. The four columns and the retention times of the fractions were as follows: (1) 5% OV-101 (Applied Science, State College, Pa.) on Chromosorb WAW-DMCS 100/120 mesh, 3 m $\times$ 7.5 mm (o.d.) glass, 90° C. for 30 min, then 4° C./min until 140° C., 5-25 min, 25-27 min, 27-60 min; (2) 4% Carbowax 20M (Applied Science, State College, Pa.) on Chromosorb WAW-DMCS 100/120 mesh, 6.1 m $\times$ 6.4 mm (o.d.) glass, 120° C. for 20 min, then 4.C/min until 140° C., 0-9 min, 9-15 min, 15-24 min; (3) 5% FFAP (Supelco, Inc., Bellefonte, Pa.) on Chromosorb G-H.P., 100/120 mesh, 3 m $\times$ 6.4 mm (o.d.) glass, 130° C. isothermal, 0-24.5 min, 24.5-26.5 min, 26.5-29 min, 29-40 min; (4) 6% TCEP (Supelco, Inc., Bellefonte, Pa.) on Chromosorb WAW-DMCS 100/120 mesh, 80.C initial, then 4°

C./min until 110.C, 33–38 min, 38–43 min, 43–56 min, 56–66 min. For all the columns, the carrier gas was nitrogen (60 ml/min), the injector temperature was 150.C, and the F.I.D. temperature was 160° C. Active fractions were analyzed by injection on BP-1, 50 m×0.33 mm (i.d), at 45° C. for 1 min, then 5° C./min until 200° C. in a Hewlett Packard 5890 gas chromatograph to determine the number of compounds present. The enantiomeric composition of ipsdienol in Fraction 2 (OV-101) was determined by the method of Slessor et al. (17).

Chemical analyses. Volatiles were analyzed by injection on BP-1, 50 m×0.33 mm (i.d), at 45° C. for 1 min, then 1° C./min until 200° C. in a Hewlett Packard 5890 gas chromatograph. Ipsdienol and lanierone peaks were identified by coinjection with synthetic samples and by GC-MS using selective ion monitoring (m/z 109) in a Finnigan Model 4500 fitted with a 30 m SPB-5 capillary column (Supelco, Inc., Bellefonte, Pa.), and with the injector temperature set at 250° C. Coupled gas chromatography-mass spectrometry was performed on a Finnigan Model 4500 fitted with a 30 m SPB-5 capillary column (Supelco, Inc., Bellefonte, Pa.), run in splitless mode, and with the injector temperature set at 250° C. All samples were run at 70 eV.

An infrared spectrum of natural lanierone was obtained on a Hewlett Packard 5965A fourier transform infrared spectrometer coupled to a Hewlett Packard 5890 gas chromatograph fitted with an HP-5 capillary column (25 m×0.3 mm i.d.).

A proton nuclear magnetic resonance spectrum of about 5 μg of pure natural lanierone was obtained on a GN 500 MHz NMR spectrometer in $D_6C_6$ with a pulse sequence to suppress solvent and water peaks.

Synthesis of lanierone. Preparation of 4,4,6-trimethyl-2-hydroxy-2,5-cyclohexadiene-1-one. Lanierone was synthesized using the method of Frimer et al. (6). Isophorone (Aldrich Chemical Co.) (3,5,5-trimethyl-2-cyclohexene-1-one), (3.0 g, 21.74 mmol), 18-crown-6 (Aldrich Chemical Co.) (8.62 g, 32.60 mmol) and potassium superoxide (Aldrich Chemical Co.) (6.18 g, 86.96 mmol) were dissolved in 30 ml benzene and stirred under dry argon for 2 hours. Water (50 ml) was added and the solution was acidified with 6N hydrochloric acid. The product was extracted with methylene chloride, washed with water, saturated sodium bicarbonate, and dried over sodium sulfate. The solvent was removed in vacuo to yield the crude product (3.55) as an oil which was purified by flash column chromatography (20) using 20% ethyl acetate in hexane to yield lanierone (1.14g, 7.5 mmol, 35%). The enol was recrystallized from hexane as white needles with a melting point of 59°–60° C. MS m/z (% rel. inten.): 152 ($M^+$, 30.20), 137 ($M^+$-$CH_3$, 28.10), 124 ($M^+$-CO, 52.00), 109 ($M^+$—$CH_3$—CO, 100). $^1$H-NMR ($C_6D_6$): δ6.71 (s, 1H, OH), 6.10 (m, J=2.8 Hz, $J_{allylic}$=1.4 Hz, 1H), 5.85 (d, J=2.8 Hz, 1H), 1.85 (d, $J_{allylic}$=1.4 Hz, 3H), 0.80 (s, 6H). $^{13}$C-NMR ($C_6D_6$): δ182.17, 154.87, 145.94, 130.85, 124.40, 36.60, 26.96, 15.26.

Laboratory bioassays. Female beetles were tested in groups of 10 in a modified Wood and Bushing (23) choice olfactometer. Positive responses were scored when a beetle showed clear orientation in an airstream for at least 3 cm before coming within 5 mm or contacting the pipette. When testing fractions, each group of ten beetles was used for each stimulus or combination of stimuli being compared. The order in which stimuli were presented was randomized between groups of beetles to minimize possible interaction effects. The raw bioassay data were analyzed by ANOVA and decisions were made at the P<0.05 level. The OV-101 fractions were assayed at dilutions equal to 1.0, 0.1, 0.01 and 0.001 of an amount of starting material containing 1 μg ipsdienol. All subsequent fractions were assayed with 1 μg synthetic racemic ipsdienol added. The concentrations of test fractions were increased at two steps in the sequence to compensate for material lost during collection.

When synthetic materials were tested, each group of ten beetles was used once, then discarded. The test stimuli were pentane (negative control), synthetic racemic ipsdienol (1 μg), lanierone (10 ng), ipsdienol plus lanierone (1 μg+10 ng), and male volatiles (second aeration; 1 μg+10 ng). The raw data (homoscedastic; Bartlett's test, P>0.05) were analyzed by one-way ANOVA followed by the LSD range test.

Field experiments. Field experiments were conducted in a mixed stand of red and scots (*P. sylvestris* L.) pine, 25 km south of Syracuse, N.Y. The purpose of the first experiment was to determine the attractiveness of lanierone using treatments similar to those of the laboratory bioassays. The treatments were: (1) hexane, (2) male volatiles (Aeration 2; 1.0 mg natural ipsdienol, 10 μg lanierone), (3) synthetic racemic ipsdienol (1.0 mg) and synthetic lanierone (10 μg), (4) synthetic lanierone (100 μg), (5) synthetic racemic ipsdienol (10 mg), (6) synthetic racemic ipsdienol (10 mg) and synthetic lanierone (100 μg), and (7) 20 male beetles in a red pine log. Treatments (1) through (6) were placed in 3.7 ml polyethylene vials with a 1 mm hole in the cap and the total volume including solvent (hexane) was 1 ml. The release rate of ipsdienol in treatments (5) and (6) was estimated to be about 67 μg/day. The release rate was determined by aerating the release device (N=3), collecting volatiles on Porapak Q over 7 days at 22° C., and quantifying by injection on capillary GC. Baits were covered with aluminum foil for protection from sunlight. Chemical baits were hung in 8-unit multiple funnel traps (11) (supplied by Phero Tech Inc., Delta, B.C.) from the lower middle funnel; logs with male beetles were hung adjacent to the lower middle funnels. The treatments were randomized in ten rows. Traps were spaced at a minimum distance of 20 m. Due to the limited quantity of male volatiles (5 mg ipsdienol) only five replicates of treatment (2) were possible; all other treatments received ten replicates. The experiment was conducted from 26 Jul. to 1 Aug., 1990.

The purpose of the second field experiment was to determine the effect of varying the amount of lanierone relative to a fixed amount of ipsdienol. The treatments were the following amounts of lanierone in combination with synthetic racemic ipsdienol (10 mg): 10 mg, 1.0 mg, 0.1 mg, 0.01 mg, and 0.001 mg. In addition, there were two controls: hexane, and 20 male *I. pini* boring in a red pine log. The seven treatments were arranged in a randomized complete block design with ten replicates. Traps were spaced at a minimum distance of 20 m. The experiment was conducted from 10–16 Aug., 1990 at the same location as the first field experiment.

RESULTS

Isolation. The concentrated Porapak Q extract from Aeration 1 contained 20 mg of ipsdienol as determined by comparison with a synthetic standard on capillary GC. A dose of the extract containing 1 μg ipsdienol elicited 67% positive response in the laboratory bioassay (FIG. 1). Fractionated material for the laboratory bioassays was quantified in the following manner. Because the starting material contained 20 mg ipsdienol and because an aliquot of the starting material containing 1 μg (or, $5 \times 10^{-6}$ of the total) ipsdienol elicited maximal response, each fraction was diluted and tested in a fraction of $5 \times 10^{-5}$ of the total, so that the ratio of ipsdienol to the fraction of starting material was $5 \times 10^{-6}$: $5 \times 10^{-6}$, or 1:1.

The three fractions from OV-101 were collected so that F1 contained all peaks eluting before ipsdienol, F2 contained one large ipsdienol peak, and F3 contained all peaks eluting after ipsdienol. A GC-MS analysis of F2 detected no significant (<1.0%) impurities. In bioassays comparing the extract, F2, and synthetic racemic ipsdienol, F2 was not significantly less attractive than the extract (P<0.05, ANOVA) at all but the $10^{-2}$ dilution (FIG. 1). Ipsdienol was significantly less attractive than the extract at all but the lowest concentration and was significantly less attractive than F2 at the two higher concentrations. The enantiomeric composition of ipsdienol in F2 was 46%(−):54%(+). Applicants found that there were no significant differences in response in the field to 30, 40, 50 and 60% (−)-ipsdienol. Therefore, the small difference in enantiomeric composition between F2 and synthetic racemic ipsdienol is insufficient to account for the difference in laboratory responses.

Figure 2:
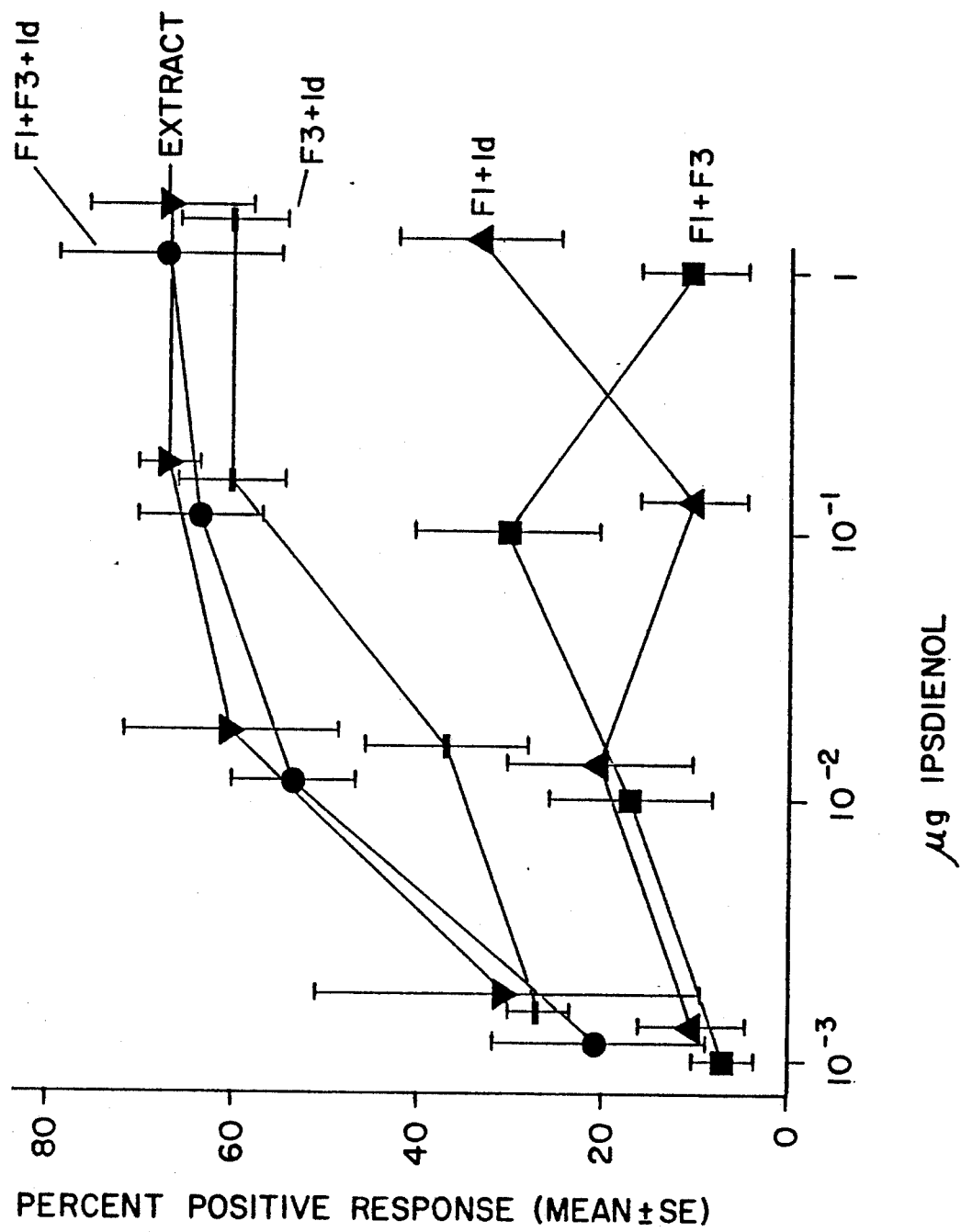
FIG. 2 is the percent positive response by female *I. pini* in laboratory bioassays of starting extract (Aeration 1), and OV-101 fractions 1 (F1) and 3 (F3). Stars indicate significant differences between stimuli and the extract (P<0.05; LSD test). (N=30 beetles at each concentration; concentrations are µg ipsdienol). Id=ipsdienol.

Further bioassays of the OV-101 fractions (FIG. 2) showed that F3 and recombined F1+F3, each in combination with ipsdienol in a 1:1 ratio, were not significantly less attractive than the extract at all dilutions. Fraction 1 in combination with ipsdienol was significantly less attractive than the extract at the $10^{-2}$ and $10^{-1}$ dilutions, and less attractive (P=0.07, ANOVA) than the extract at the highest concentration. The recombined F1+F3 without ipsdienol added was significantly less attractive than the extract at all but the lowest concentration. Because the largest differences between stimuli occurred at the higher concentrations, subsequent bioassays utilized the single highest concentration (i.e., 1 μg ipsdienol).

Figure 3:
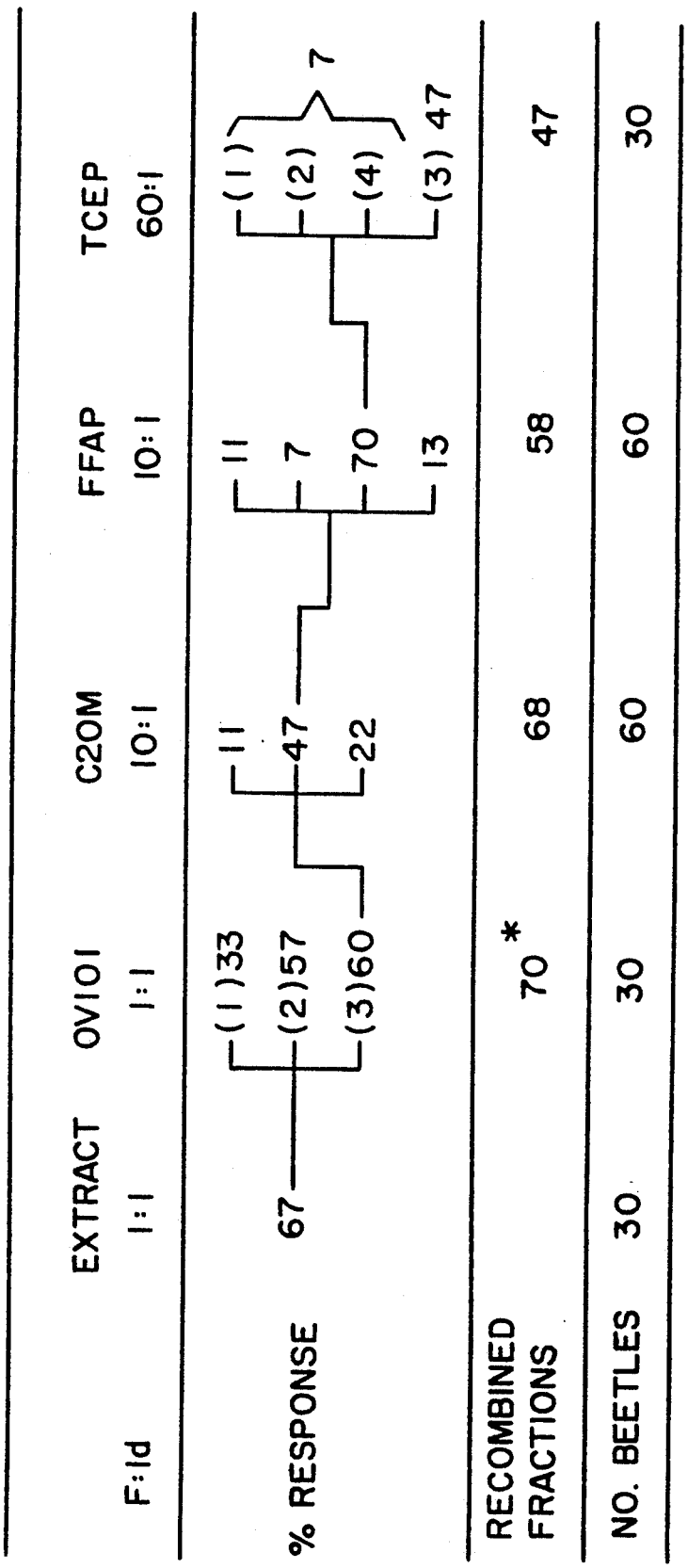
FIG. 3 is a summary of laboratory bioassay data on four sequential fractionations of Porapak Q collected volatiles from 1040 male *Ips pini* (Aeration 1). The numbers in parentheses are referenced in the text. F:Id=ratio of fraction to ipsdienol. Quantification of fractions is based on the quantity of ipsdienol (20 mg) in the starting material (i.e., 1 µg ipsdienol is equal to 1 µg/20 mg, or $5 \times 10^{-5}$ of the total; see text). *GC total

Only one C20M fraction (F3.2) in combination with ipsdienol elicited a level of response (47%) that was not significantly less attractive than that of the recombined fractions (68%) (FIG. 3). When this fraction was refractionated on FFAP, again, only one fraction (F3.2.3) was not significantly less attractive (70%) than the recombined fractions (58%). The concentration of the fractionated material used in the assays was increased ten fold in order to maintain levels of response comparable to those of the extract. The need to increase concentration is attributable to material losses incurred in the GC fractionation.

Of the TCEP fractions, F1, F2, and F4, when recombined, elicited a significantly lower level of response (7%) than all four fractions recombined (47%) (FIG. 3). Fraction 3 elicited the same level of response (47%) as all four fractions recombined. Fraction 3 alone and the recombined F1, F2, and F4 were assayed in this configuration because F3 manifested a characteristic odor that we had detected in all previous attractive fractions and the extract. Again, the concentration was increased (six fold) in order to maintain a satisfactory level of response. Capillary GC analysis of F3.2.3.3 revealed the presence of a single peak.

Figures 4A, 4B:
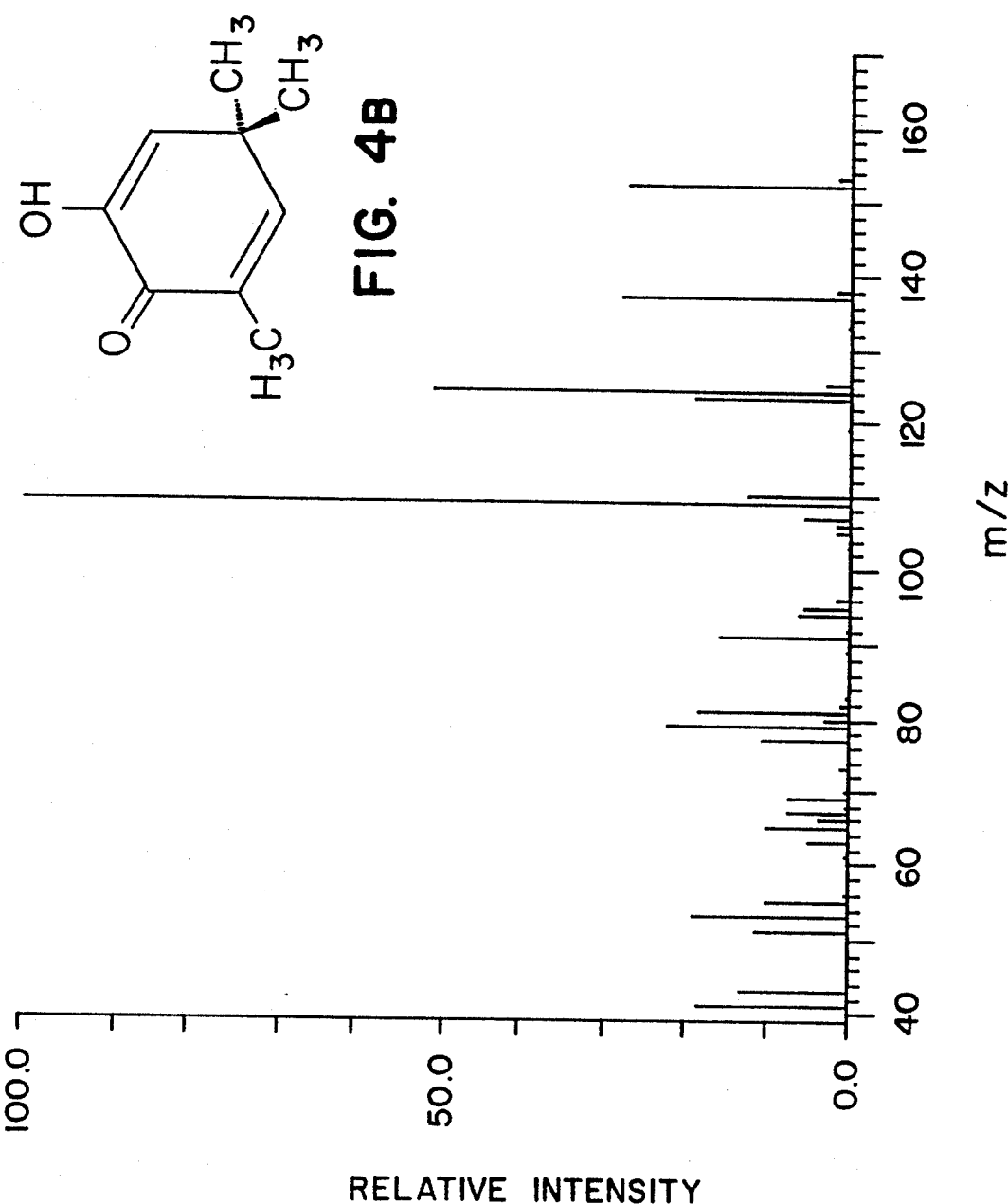
FIG. 4 is a mass spectrum of natural lanierone isolated from Porapak Q collected volatiles from 1040 male *Ips pini* (Aeration 1), and shows the structure of lanierone isolated from Porapak Q collected volatiles from 1040 male *Ips pini* (Aeration 1).

Identification. In the mass spectrum of the compound in F3.2.3.3 (FIG. 4), the M+ ion was judged to be m/z 152. The next highest fragment ion was 137, M+—CH3.

Assuming that there is only C, H, and O present, three likely molecular formulae were $C_{10}H_{16}O$, $C_9H_{12}O_2$, and $C_8H_8O_3$.

Figure 5:
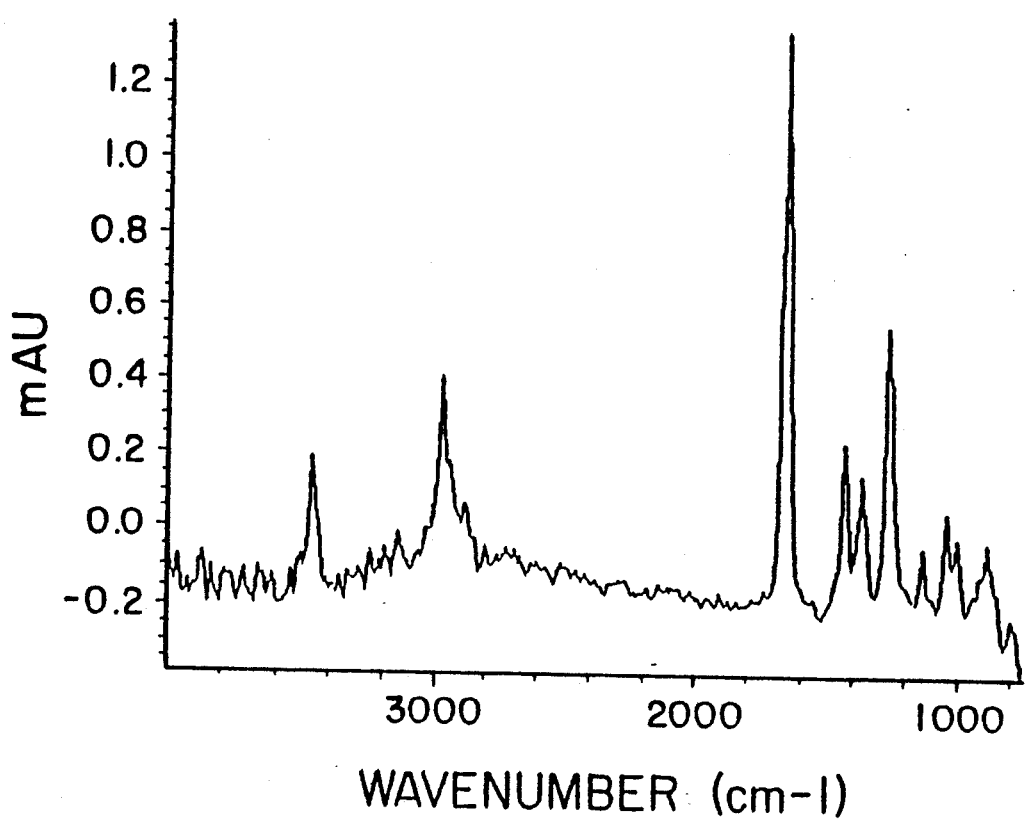
FIG. 5 is an infrared spectrum of lanierone isolated from Porapak Q collected volatiles from 1040 male *Ips pini* (Aeration 1).

The FT-IR spectrum (FIG. 5) indicated absorptions at 3462 v OH, 2974 v CH3, 1659 v C=O, 1434 $\delta_s$ CH3, 1367 $\delta_s$ CH3, and 1264 v C—O, cm$^{-1}$. The presence of two types of oxygen containing functional groups excludes the molecular formula $C_{10}H_{16}O$.

Figure 6:
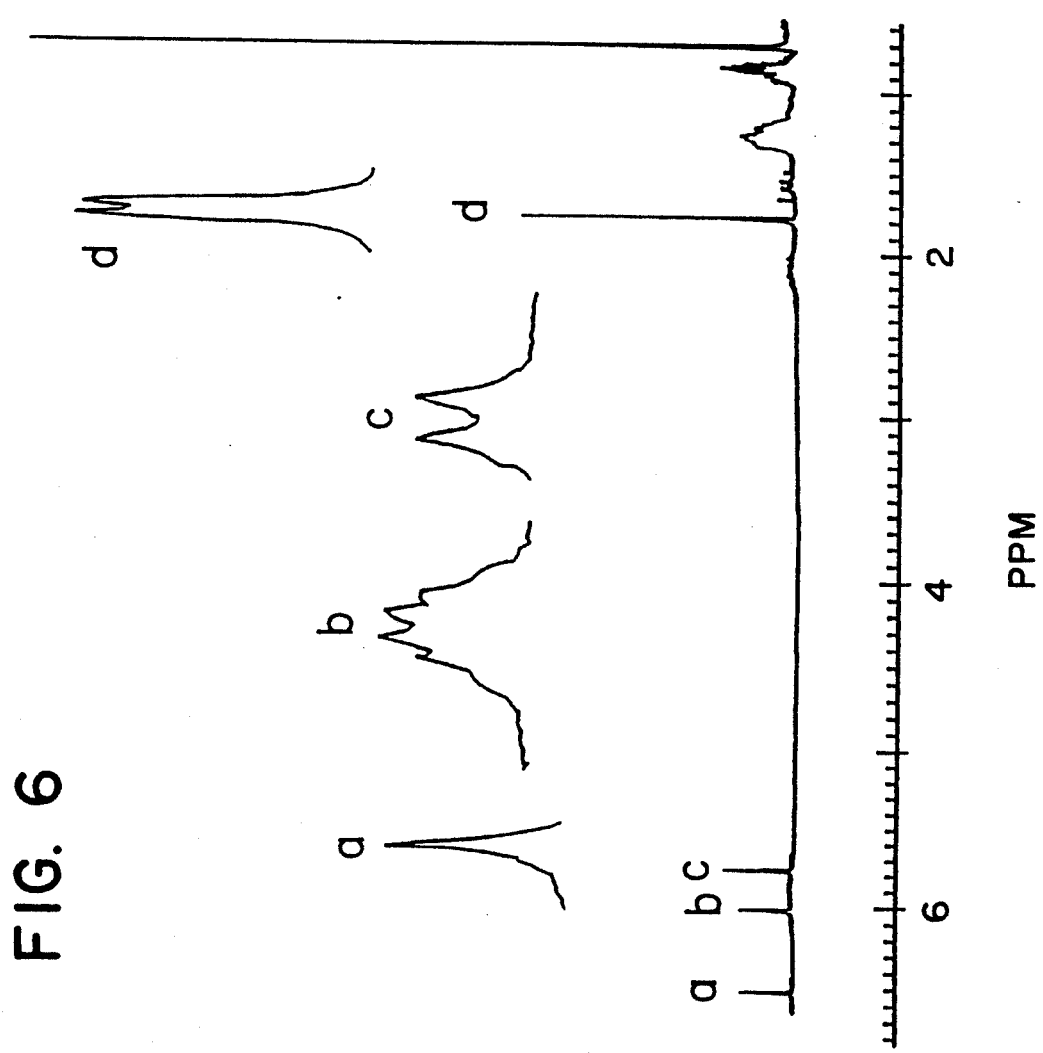
FIG. 6 is an NMR spectrum of natural lanierone isolated from Porapak Q collected volatiles from 1040 male *Ips pini* (Aeration 1).

The $^1$H NMR spectrum is shown in FIG. 6. The singlet at δ0.70 (6H) indicates that there are two identical methyl groups on a quaternary carbon (no coupling); the doublet at δ1.80 (3H) indicates a methyl group on an olefinic carbon; the doublet at δ5.78 (1H) and the multiplet at δ6.03 (1h) indicate protons on olefinic carbons; and the singlet at δ6.53 (1H) is a hydrogen bonded hydroxyl proton. The indication of three methyl groups (9H) excludes the molecular formula $C_8H_8O_3$. On the basis of the MS, IR, and NMR spectra of the natural and the synthetic compound, the structure was determined to be 4,4,6-trimethyl-2-hydroxy-2,5-cyclohexadiene-1-one (FIG. 7).

Analyses of beetle aerations. On the normal-scale GC trace (FIG. 7) of Aeration 2, ipsdienol was represented by a peak that was small relative to several others, representing host volatiles. Only when the scale was increased 100 fold did the lanierone peak become apparent (FIG. 7, inset). A comparison of peak areas revealed that the ratio of lanierone to ipsdienol was 1:500 (0.2%).

Figure 8A:
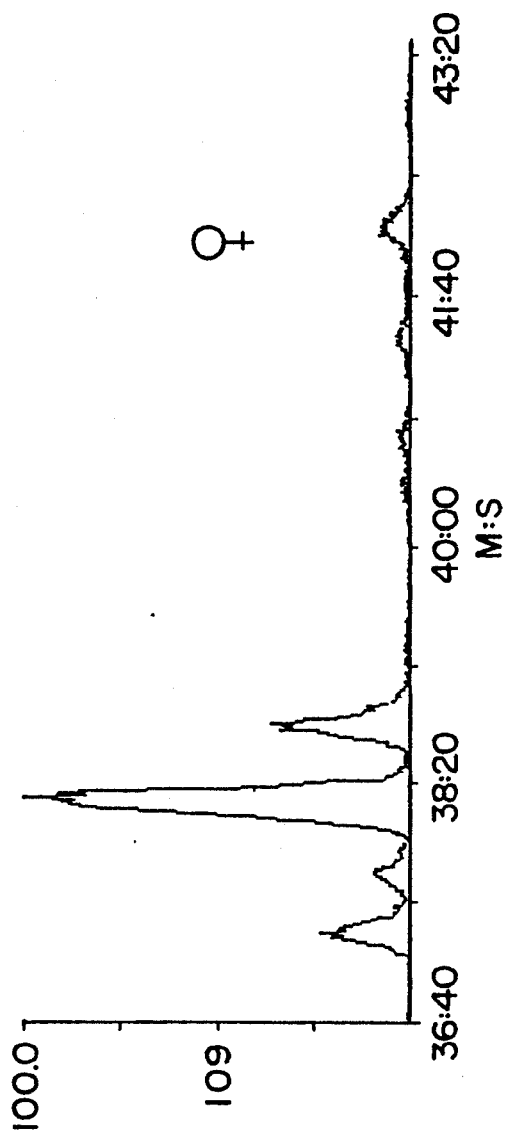
FIG. 8 is a selective ion monitoring mass spectra (m/z 109) of male volatiles (top) and female volatiles (bottom). Note that peak sizes are not proportionate because m/z 109 is the base peak for lanierone, but only a minor fragment for ipsdienol. See text for details.
Figure 8B:
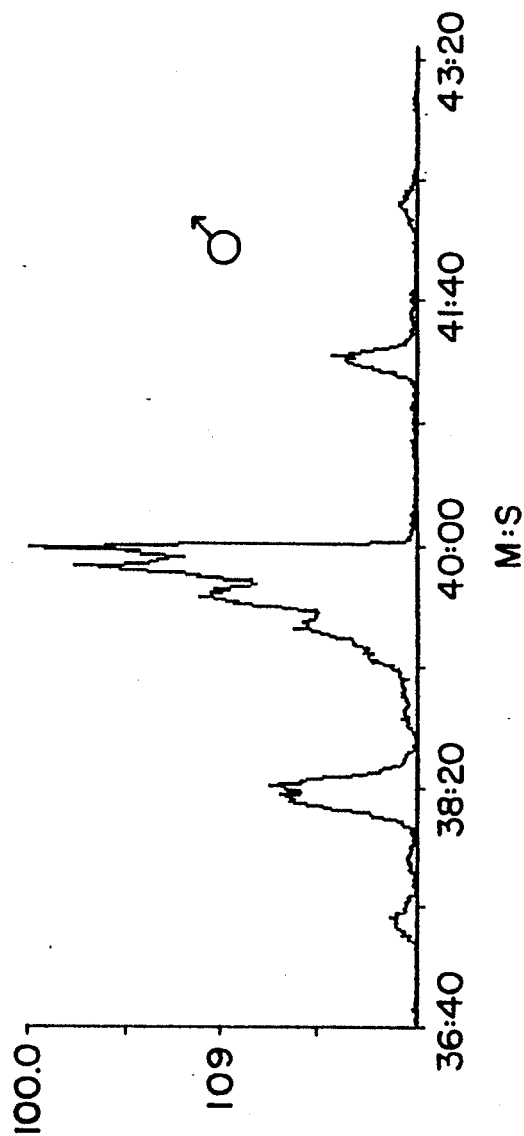

The selective ion monitoring mass spectra (m/z 109) of the male and female aerations (FIG. 8) revealed both ipsdienol and lanierone in the male extract but neither compound in the female extract. Because the female (and male) aeration was made with beetles feeding on host material (red pine), and no lanierone was collected, lanierone must not be produced by the host nor females. Rather, lanierone is exclusively male-produced.

Figure 9:
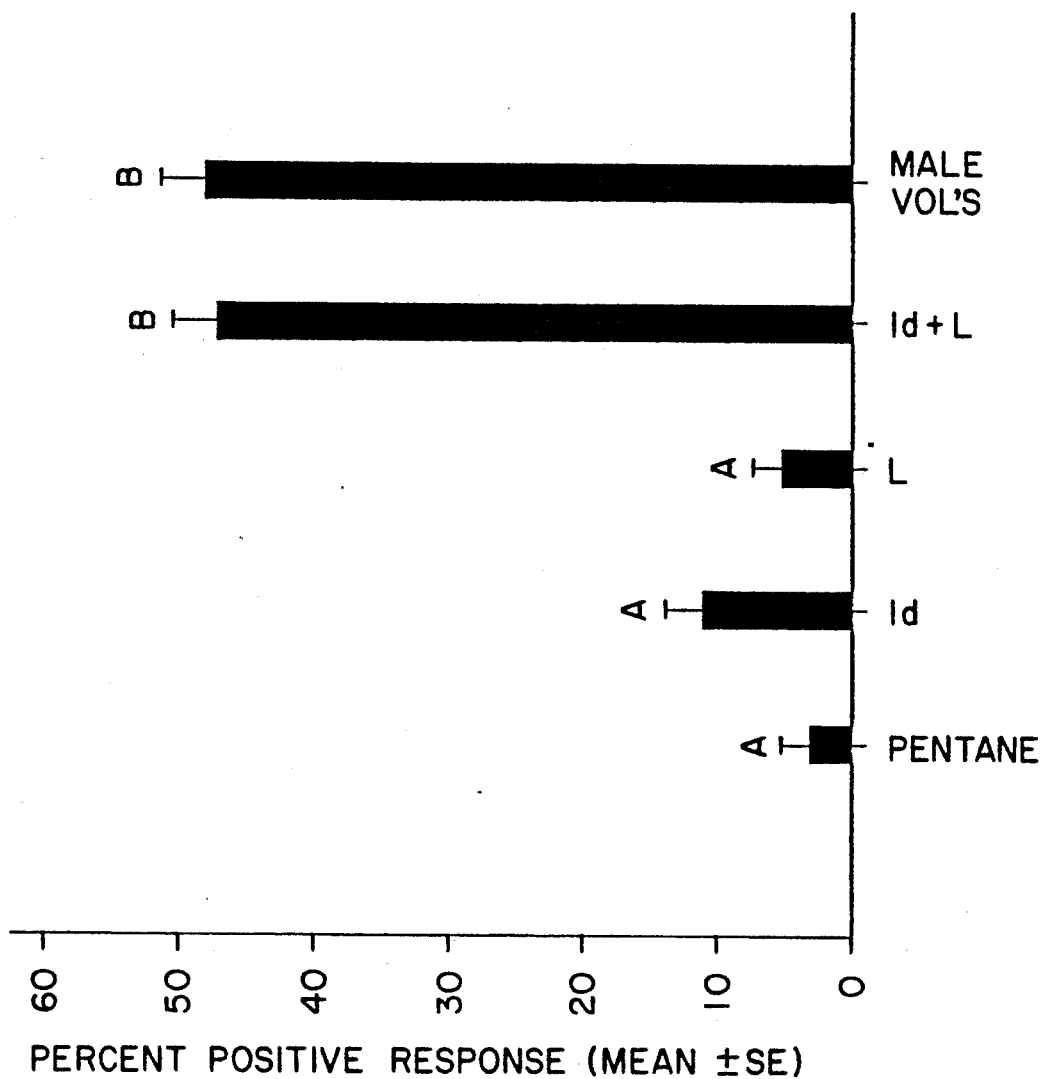
FIG. 9 is the percent positive response in the laboratory bioassay by female *I. pini* to synthetic lanierone and ipsdienol. Id=ipsdienol; L=lanierone; male vol's=male volatiles from Aeration 2 (see text for details). Different letters over bars indicate significant differences (ANOVA on raw data followed by LSD range test).

Laboratory bioassays. In laboratory bioassays, neither synthetic compound alone was significantly more attractive to females than the solvent (pentane) control (FIG. 9) (P>0.05; ANOVA followed by LSD range test). The male volatiles and the combination of synthetic ipsdienol (1 μg) and synthetic lanierone (10 ng) were significantly more attractive than the solvent control, ipsdienol, and lanierone alone. There was no significant difference between the levels of attraction elicited by the male volatiles and the combination of synthetic ipsdienol and synthetic lanierone. These data indicate that ipsdienol and lanierone function in a synergistic manner.

Figure 10:
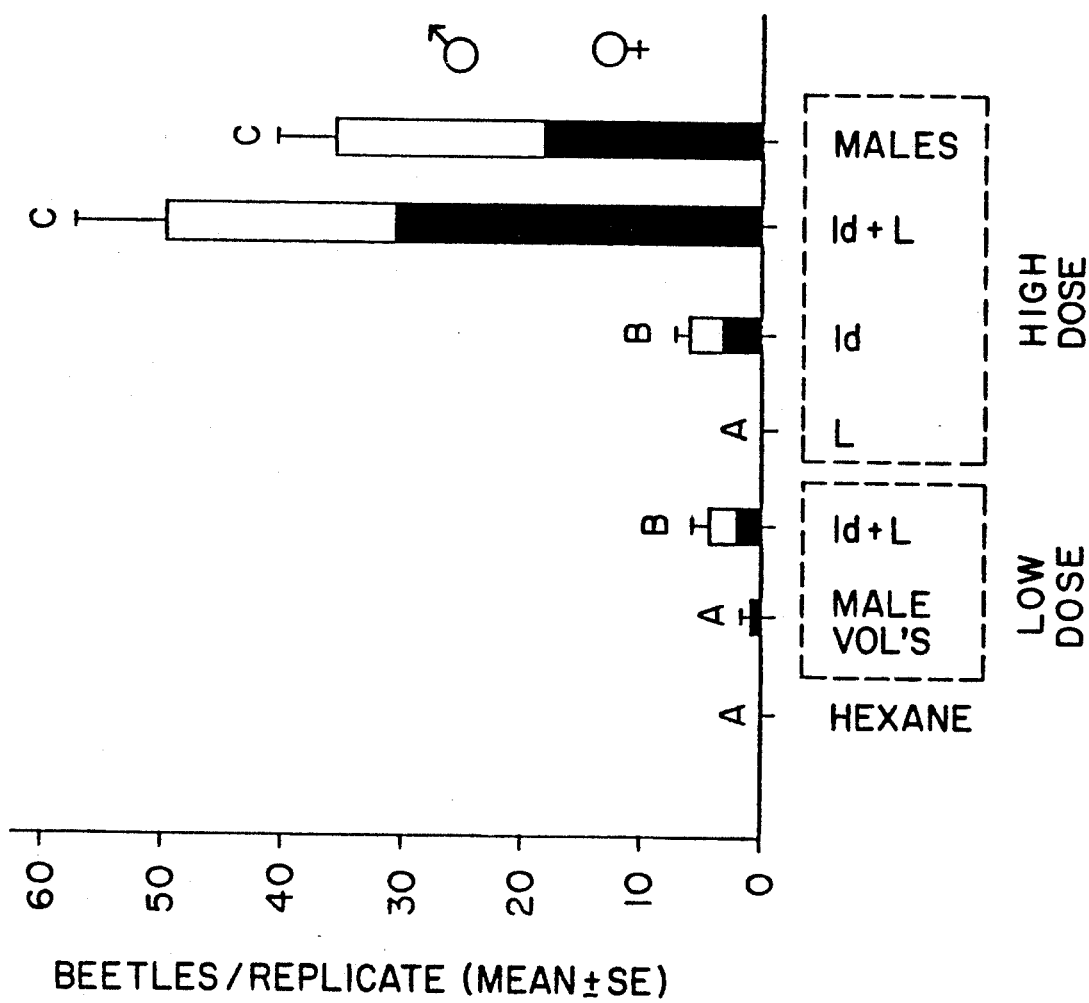
FIG. 10 is the field test of lanierone at two doses 25 km south of Syracuse, N.Y., 26 Jul. to 1 Aug., 1990. Id=ipsdienol; L=lanierone; male vol's=male volatiles (Aeration 2, see text); males=20 males boring in a red pine log. Low dose: Id=1 mg; L=0.01 mg. High dose: Id=10 mg; L=0.1 mg. Different letters over bars indicate significant differences (ANOVA on Log(Y+1) transformed data followed by LSD range test).

Field experiments. The treatments of the first field experiment fell into three homogeneous groups (FIG. 10; P<0.05; ANOVA on log(Y+1) transformed data followed by LSD range test): (1) hexane control, male volatiles and lanierone, (2) ipsdienol plus lanierone (low dose) and ipsdienol (high dose), and (3) ipsdienol plus lanierone (high dose) and males. The large number of beetles attracted by ipsdienol plus lanierone (high dose) compared to the small numbers attracted by ipsdienol and lanierone alone support applicants' laboratory result that these two compounds function in a synergistic, rather than an additive, manner. The sex ratios varied significantly between the ipsdienol plus lanierone (high dose) (m/f+m=0.38) and the male beetle (m/f+m=0.49) treatments (P<0.01, test for population proportions [12]).

The male volatiles collected by aeration on Porapak Q (Aeration 2) contained amounts of ipsdienol and lanierone equal to those of the synthetic mixture. Therefore, the small number of beetles attracted by the male volatiles must have been due to the presence of large quantities of terpenes from the aerated host material, the presence of microbial oxidation products, insufficient replication (N=5 for the male volatile treatment, for all others N=10), or other factors.

Figure 11:
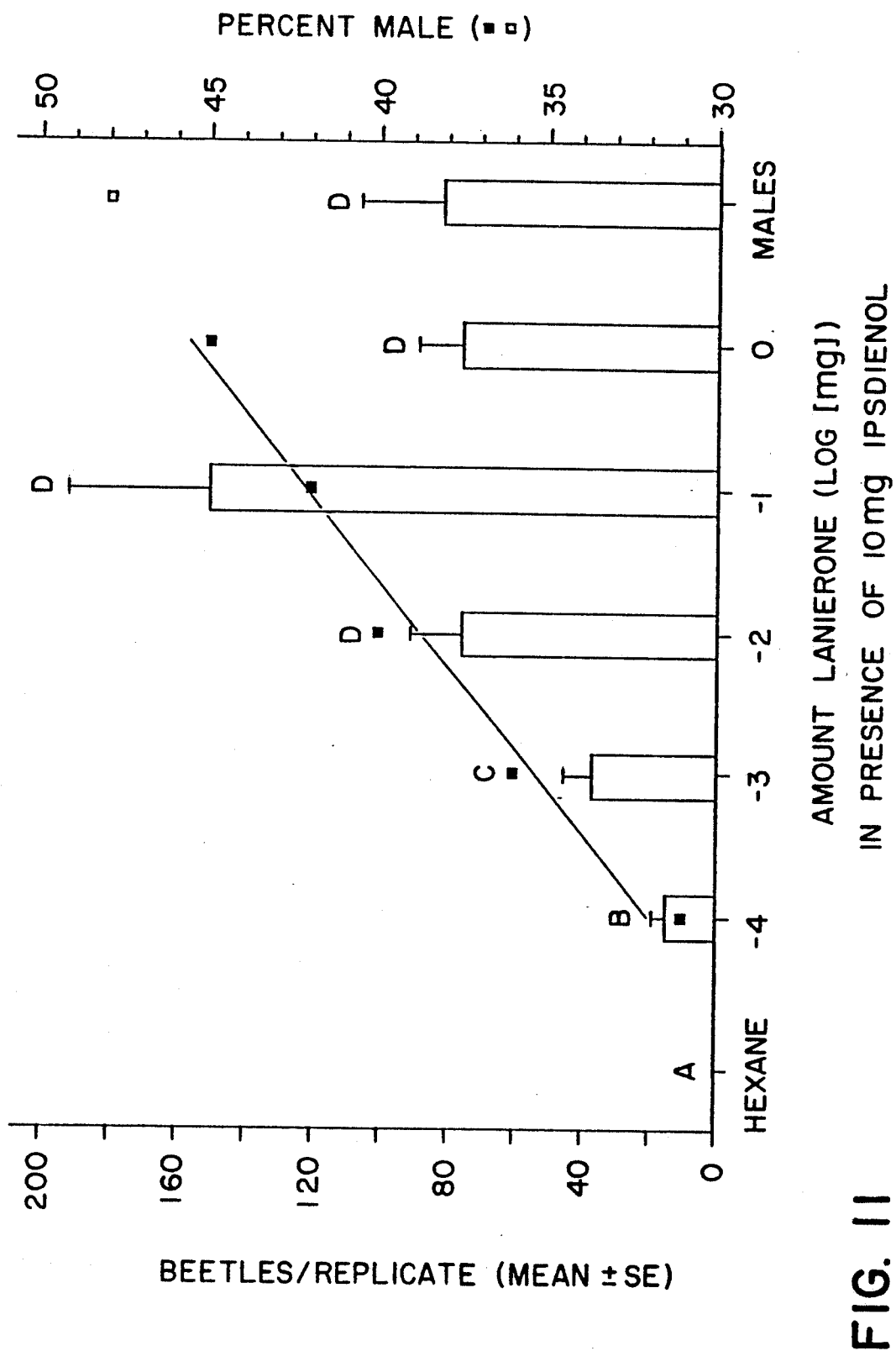
FIG. 11 shows the effect of varying the proportion of lanierone with a fixed amount (10 mg) of ipsdienol on the mean number (left axis, bars) and percent male (right axis, regression) of *I. pini* trapped in multiple-funnel traps 25 km south of Syracuse, N.Y., Aug. 10–16, 1990. Different letters over bars indicate significant differences among mean numbers of beetles trapped (ANOVA on Log(Y+1) transformed data followed by LSD range test). For the regression of sex ratio on proportion of lanierone, $R^2=0.97$, $P=0.002$, $Y=3.4 \text{Log} X+45.6$.

In the second field experiment, the amount of lanierone had a significant effect on the numbers of beetles trapped (FIG. 11). The three higher doses together with the male treatment formed a homogeneous group (P>0.05; ANOVA on log(Y+1) transformed data followed by LSD range test). The treatment with 0.01 mg lanierone in combination with 10 mg ipsdienol attracted fewer beetles than the higher doses, but more than the solvent control and the lowest dose. The lowest dose (0.001 mg lanierone) attracted significantly more than the solvent control. There was a close relationship between the sex ratio of responding beetles and the quantity of lanierone in the presence of 10 mg ipsdienol ($R^2=0.97$, $P=0.002$; FIG. 12).

Although certain preferred embodiments have been depicted and described in detail herein, it will be apparent to those skilled in the relevant art that various modifications, additions, substitutions and the like can be made without departing from the spirit of the invention, and these are therefor considered to be within the scope of the invention as defined by the appended claims.

REFERENCES

1. Birch, M. C. et al., J. Chem. Ecol. 6:703-717 (1980).
2. Birgersson, G. et al., J. Chem. Ecol. 10:1029-1055 (1984).
3. Brownlee, R. G., and Silverstein, R. M., Anal. Chem. 40:2077-2079 (1968).
4. Byers, J. A. et al., J. Chem. Ecol. 16:861-876 (1990).
5. Byrne, K. J. et al., J. Chem. Ecol. 1:1-7 (1975).
6. Frimer, A. A. et al., J. Org. Chem. 54:4853-4866 (1989).
7. Greis, G. et al., J. Econ. Entomol. 81:1715-1720 (1988).
8. Lanier, G. N. et al., Can. Entomol. 104:1917-1923 (1972).
9. Lanier, G. N. et al., J. Chem. Ecol. 3:1-8 (1977).
10. Lanier, G. N. et al., J. Chem. Ecol. 6:677-687 (1980).
11. Lindgren, B. S., Can. Entomol. 115:299-302 (1983).
12. Mendenhall, W., *Introduction to probability and statistics*. Prindle, Weber and Schmidt, Boston, Massachusetts (1983).
13. Miller, D. R. and Borden, J. H., J. Chem. Ecol. 16:2519-2531 (1990).
14. Miller, D. R. et al., Can. Entomol. 122:401-406 (1990).
15. Moeck, H. A., Can. Entomol. 102:792-796 (1970).
16. Silverstein, R. M. et al., J. Econ. Entomol. 60:944-949 (1967).
17. Slessor, K. N. et al., J. Chem. Ecol. 11:1659-1667 (1985).
18. Smith, A. B. et al., Science 228:175-177 (1985).
19. Stewart, T. E., "Volatiles isolated from *Ips pini*: Isolation, identification, enantiomeric composition, biological activity." MSc thesis. College of Environmental Science and Forestry, SUNY, Syracuse, N.Y. (1975).
20. Still, W. C. et al., J. Org. Chem. 43:2923-2925 (1978).
21. Vité, J. P., Science 156:105 (1967).
22. Vité, J. P. and Renwick, J. A. A., Contrib. Boyce Thompson Inst. 24:323-328 (1970).
23. Wood, D. L. and Bushing, R. W., Can. Entomol. 95:1066-1078 (1963).

What is claimed is:

1. A synthetic composition comprising 4,4,6-trimethyl-2-hydroxy-2,5-cyclohexadiene-1-one, 2-methyl-6-methylene-octa-2,7-dien-4-ol, and a suitable carrier.
2. The synthetic composition of claim 1, wherein the weight ratio of the amount of 4,4,6-trimethyl-2-hydroxy-2,5-cyclohexadiene-1-one to the amount of 2-methyl-6-methylene-octa-2,7-dien-4-ol is effective to control or attract bark beetles.
3. The synthetic composition of claim 2, wherein the weight ratio comprises about 1 g:100 g.
4. The composition of claim 2 further comprising an amount of a control agent effective to eliminate or control the reproduction of said bark beetle.
5. The composition of claim 4, wherein said control agent comprises an insecticide for the bark beetle.
6. An attractant composition for bark beetle *Ips pini* comprising a mixture of the compounds 4,4,6-trimethyl-2-hydroxy-2,5-cyclohexadiene-1-one and 2-methyl-6-methylene-octa-2,7-dien-4-ol in a ratio of 1:100, and a suitable carrier, wherein the composition acts as an attractant for the bark beetle.
7. A method of attracting bark beetles to a locus for the monitoring or control of reproduction of said bark beetles, comprising applying to said locus an effective amount of the composition of claim 1, and thereby attracting said bark beetles to said locus.
8. A method of attracting bark beetles to a locus for the elimination or control of reproduction of said bark beetles, comprising applying to said locus an effective amount of the composition of claim 4, and thereby attracting said bark beetles to said locus.
9. A method of trapping and tree baiting bark beetles, comprising applying the composition of claim 1 to trees in a concentration which is effective to attract said bark beetles to a region frequented by said bark beetles, and thereby attracting said bark beetles so as to trap said bark beetles.
10. The method of claim 9, wherein the weight ratio of the amount of 4,4,6-trimethyl-2-hydroxy-2,5-cyclohexadiene-1-one to the amount of 2-methyl-6-methylene-octa-2,7-dien-4-ol comprises about 1 g:100 g.

* * * * *